United States Patent
Vignot

(10) Patent No.: US 6,440,909 B1
(45) Date of Patent: Aug. 27, 2002

(54) CLEANING ARTICLE USED IN THE ABSENCE OF A WATER SOURCE

(75) Inventor: Eric Vignot, Mitry Mory (FR)

(73) Assignee: Laboratories Prodene Klint, Mitry-Mory (FR)

( * ) Notice: Subject to any disclaimer, the term of this patent is extended or adjusted under 35 U.S.C. 154(b) by 0 days.

(21) Appl. No.: 09/544,489

(22) Filed: Apr. 7, 2000

(30) Foreign Application Priority Data

Apr. 9, 1999 (FR) .............................. 99 04442

(51) Int. Cl.$^7$ .......................... C11D 17/04; C11D 3/20; C11D 3/43
(52) U.S. Cl. ....... 510/130; 510/138; 510/143; 510/157; 510/174; 510/214; 510/241; 510/365; 510/366; 510/438; 510/439
(58) Field of Search ................. 510/130, 138, 510/143, 157, 438, 439, 174, 214, 241, 365, 366

(56) References Cited

U.S. PATENT DOCUMENTS

| | | | |
|---|---|---|---|
| 5,320,772 A | | 6/1994 | Tricca ....................... 252/160 |
| 5,683,971 A | | 11/1997 | Rose et al. .................. 510/130 |
| 5,891,835 A | * | 4/1999 | Vlasblom .................... 510/143 |
| 5,910,455 A | * | 6/1999 | Maddern et al. ............... 442/60 |
| 5,941,378 A | * | 8/1999 | Rose et al. .................. 206/205 |
| 5,951,991 A | * | 9/1999 | Wagner et al. ............... 424/401 |
| 5,972,361 A | * | 10/1999 | Fowler et al. ............... 424/402 |
| 6,015,763 A | * | 1/2000 | Vlasblom .................... 442/123 |
| 6,063,390 A | * | 5/2000 | Farrell et al. ............... 424/404 |
| 6,063,397 A | * | 5/2000 | Fowler et al. ............... 424/443 |

FOREIGN PATENT DOCUMENTS

| | | | |
|---|---|---|---|
| EP | 0919613 | * | 6/1999 |
| GB | 618075 | | 2/1949 |
| WO | 98/12958 | * | 4/1998 |
| WO | 98/12959 | * | 4/1998 |

* cited by examiner

*Primary Examiner*—Lorna M. Douyon
(74) *Attorney, Agent, or Firm*—Young & Thompson

(57) ABSTRACT

A cleaning article used in the absence of a water source, comprises an abrasive substrate and a liquid impregnating it. The substrate is a non-woven abrasive material such as a sheet of plastic fibers and the impregnation liquid is an aqueous solution of d-limonene, surface active agent and hydrophilic solvent with, if desired, the usual additives. Impregnation can be carried out on a stack of towels by pouring the impregnating solution onto the stack, which spreads uniformly throughout the towels.

9 Claims, No Drawings

CLEANING ARTICLE USED IN THE ABSENCE OF A WATER SOURCE

The invention relates to a cleaning article, in particular for the hands, used in the absence of a water source, comprising an abrasive substrate and a liquid impregnating it.

U.S. Pat. No. 4,833,003 discloses a stack of moist abrasive towels, the towels having at least one abrasive surface and containing any cleaning solution. The abrasive surface is obtained by projection of a melted polymer onto a polyolefin non-woven material.

U.S. Pat. No. 5,683,971 discloses abrasive articles for cleaning the hands, comprising a substrate as before, and a hand cleaning emulsion impregnated into the substrate and comprising 2 to 40% of an organic emulsifiable solvent, 2 to 20% of a surface active agent that can form a water/oil emulsion, and 60 to 95% water.

The basic non-woven materials used in these two documents have a surface appearance and quality which is very heterogeneous, which render them aggressive to the hands and which give rise to problems in their manipulation, and particularly in winding and unwinding machines that cut off the towels because the accumulation of polyolefin can cause them to seize.

The cleaning emulsion used in the second above document of the prior art contains emulsifiable organic solvents, such as mineral oil, which are irritants. Moreover, the emulsion is unstable: by gravity, there is a separation with concentration of the aggressive solvents and it is therefore necessary continuously to mix the emulsion during impregnation of the non-woven materials.

The use of an emulsion also requires the use of a specific container, namely a cabinet containing a roll of continuously connected towels with a central manifold for impregnation with emulsion.

The invention permits overcoming these drawbacks by providing a cleaning article, particularly but not exclusively for the hands, adapted to be used away from a water source, which will not be aggressively abrasive, which contains no irritating solvents, which requires no continuous mixing of the impregnation liquid and which will not be limited to a single production and use.

The cleaning article is thus constituted by a substrate which is an abrasive non-woven substance throughout its mass and the impregnation liquid is an aqueous solution of d-limonene, surface active agents and hydrophilic solvents with, if desired, the usual additives.

The non-woven substance abrasive throughout its mass is obtained by use of a mixture of abrasive fibers selected from natural fibers, artificial fibers or synthetic fibers or mixtures, for example polyolefin fibers, for example polyethylene or polypropylene. These fibers are transformed into an abrasive substrate on their two surfaces by a conventional process for producing non-woven material. These fibers are if desired dyed in the mass if it is desired that the final towel have a particular color. A product of this type is available from AHLSTROM under the trademark SPUNLACE and is constituted of a mixture of 85% by weight of cellulose fiber (40%), viscose (10%), and polyester (35%), and 15% of binders (acrylic or the like).

The impregnation solution contains essentially an aqueous solution of d-limonene, surface active agents and hydrophilic solvents. It can also contain usual additives, such as perfume and preservatives.

The impregnation ratio is comprised between 1.5 and 4; there is meant by this ratio the ratio mass of the solution/ mass of the non-woven material.

The surface active agents can be non-ionic, amphoteric, anionic or cationic surface active agents. There can be cited by way of example the following:

anionic, LES Na (TEXAPON-HENKEL): alkylsulfosuccinate and others, non-ionic, (EUMULGIN-HENKEL): fatty alcohols and ethoxylated fatty substances and others, amphoterics, (TEGOBETAINE-GOLDSCHMIDT): betaines, propionics and others, cationic (CATIGENE-STEPHAN): quaternary ammoniums, derivatives and others.

The hydrophilic organic solvents which assist in the solubilization of d-limonene are selected from alcohols (methanol, ethanol, or higher alcohols), glycols (propylene glycol and others), organic esters and in particular dibutyl esters of glutaric, adipic, butyric acids, etc...

The following table gives the range of composition permitting obtaining an aqueous solution which will be limpid, stable and without any phase separation of the constituents over time, which shows that it is a true solution.

| Ingredients | Wide range | Narrow range | Preferred |
| --- | --- | --- | --- |
| d-Limonene | 0.05 to 0.9% | 0.5 to 0.9% | 0.9% |
| Surface active agents | 2 to 40% | 5 to 20% | 10% |
| Hydrophilic organic solvents | 8 to 30% | 8 to 15% | 9% |
| Preservative | 0.02 to 1.5% | 0.1 to 1% | 0.5% |
| Perfume | 0.1 to 1 | 0.1 to 0.5% | 0.2% |
| Water | 26 to 90 | 64 to 87% | 79.4% |

% by weight of the solution

EXAMPLE OF PREPARATION

A solution according to the preferred composition in the above table is prepared. Moreover, there is prepared a stack of towels from a master roll of non-woven Spunlace, of dimensions 200×350 mm, in a dispensing box of corresponding dimensions. The stack of pieces of non-woven material has a weight of 300 g.

Onto this stack, there is poured, as a function of the impregnation ratio defined above, the solution previously prepared, without it being necessary to agitate it, and it is permitted to diffuse throughout all the pile of towels. At the end of several minutes, the towels are uniformly impregnated with the solution and this impregnation remains stable with time.

The process of impregnation of a continuous roll of towels in a dispensing cabinet can of course be used with the solution according to the invention, if it is desired to use a presentation and a dispensing of this type.

The possibility of impregnating the towels flat permits a flat presentation which permits packaging in small quantities or even individually.

It will be seen that the towels thus obtained, which contain no solvents of the mineral oil type able to attack the plastic materials, can be used not only for cleaning hands soiled with oil, tar, fresh paint, ink, ink stains from marking pens, grass stains, . . . , but also for cleaning various sensitive surfaces of the type of office machine frames and particularly computers, or various floor and wall coverings.

What is claimed is:

1. A cleaning article useful without a source of water, consisting of an abrasive substrate and an impregnation liquid, wherein the substrate is an abrasive non-woven material throughout its mass and the impregnation liquid consists of an aqueous solution of 0.5 to 0.9% by weight of d-limonene, 2 to 40% by weight of surface active agent, 8 to 30% of hydrophilic solvent and 26 to 90% of water by weight of the aqueous solution.

2. A cleaning article as claimed in claim 1, wherein the non-woven abrasive substrate is constituted by a mixture of abrasive fibers.

3. A cleaning article according to claim 2, in which the abrasive fibers are selected from the group consisting of natural fibers, artificial fibers or synthetic fibers, and a mixture thereof.

4. A cleaning article according to claim 1, in which the hydrophilic solvent is selected from the group consisting of alcohol, glycol, organic ester and glycerol.

5. A cleaning article according to claim 1, wherein the surface active agent is selected from the group consisting of non-ionic, amphoteric, cationic and anionic surface active agents.

6. A cleaning article according to claim 1, wherein the d-limolene is present in an amount of 0.9% by weight in the aqueous solution.

7. A cleaning article according to claim 1, in the form of a towel.

8. A stack of cleaning articles in the form of towels according to claim 7, in a dispensing container.

9. Process for producing a stack of cleaning articles, comprising stacking flat pieces of non-woven abrasive material with the dimensions of a towel, and impregnating the stack by pouring an impregnation liquid according to claim 1 onto the stack in an impregnation ratio comprised between 1.5 and 4.

* * * * *